United States Patent
Lei

(10) Patent No.: US 6,541,163 B1
(45) Date of Patent: Apr. 1, 2003

(54) PROCESS OF POWDER FOR BATH FROM NATURAL PLANTS

(75) Inventor: Jufang Lei, Tibet (CN)

(73) Assignee: Tibet Yutuo Institute of Tibetan Medicine, Tibet (CN)

( * ) Notice: Subject to any disclaimer, the term of this patent is extended or adjusted under 35 U.S.C. 154(b) by 0 days.

(21) Appl. No.: 09/719,310

(22) PCT Filed: Jun. 8, 1999

(86) PCT No.: PCT/CN99/00077

§ 371 (c)(1),
(2), (4) Date: Jan. 23, 2001

(87) PCT Pub. No.: WO99/64026

PCT Pub. Date: Dec. 16, 1999

(30) Foreign Application Priority Data

Jun. 11, 1998 (CN) .......................................... 98102252

(51) Int. Cl.[7] .......................... A61K 9/16; A61K 33/00; A61K 35/78
(52) U.S. Cl. ..................... 429/489; 424/725; 424/725.1
(58) Field of Search ................................ 424/489, 725, 424/725.1; 426/270

(56) References Cited

U.S. PATENT DOCUMENTS 5,445,830 A * 8/1995 Hagiwara et al. ........... 426/270

FOREIGN PATENT DOCUMENTS

| CN | A1038027 | 12/1989 |
| CN | A1038584 | 1/1990 |
| CN | 1038584 | * 1/1990 |
| CN | A1046284 | 10/1990 |

* cited by examiner

Primary Examiner—Thurman K. Page
Assistant Examiner—Blessing Fubara
(74) Attorney, Agent, or Firm—Thorpe North and Western, LLP

(57) ABSTRACT

The invention relates to a process for making medicated bath powder from natural plants. The process comprises multiple cycles of extraction with heating; combining the resulting extracts and concentrating, freezing drying or spraying drying them to form a drug powder, which then mixed with the volatile oils obtained from the first extraction. The active components of these natural plants can be effectively preserved in the medicated bath powder of the present invention.

14 Claims, No Drawings

PROCESS OF POWDER FOR BATH FROM NATURAL PLANTS

FIELD OF THE INVENTION

The present invention relates to a method for preparing a medicated bath powder, specifically to a method of processing a medicated bath powder from natural herb medicated bath liquid.

BACKGROUND OF THE INVENTION

There has been nearly a thousand year history of using Tibetan medicated bath liquor (TMBL) made by crude Tibet medicine, in China, to treat various diseases such as rheumatoid arthritis, rheumatic arthritis, psoriasis, postpartum convulsions, muscular atrophy, callosity, hemiplegia and hypertension. The therapeutic effects are remarkable and no obvious toxic actions or side effects are exhibited. Sources for the Tibetan medicines are plentiful and each of them have individual distinguishing features and are specialized for the treatment of difficult and complicated cases in Tibetan medical therapy.

The characteristics of the above-mentioned diseases are that they are chronic diseases which are hard to cure. Both ordinary Chinese Traditional therapy and Western medicine require long therapeutic courses for the treatment of these diseases, and the therapeutic effects are still not ideal. However, if these diseases are treated with from one to three courses of Tibetan medicine bath liquor, much improved therapeutic results are achieved. Recently a number of, "Sections of TMBL", have been established in many places in Tibet, Xinjiang, Inter Mongolia, Gansu, Qinghai, Sichuan and Henan. However, these hospitals are related to the source of the Tibetan medicines and most of them are set up in remote mountainous areas and county towns where limited access brings about much inconvenience for patients. Medicated bath therapy requires the patients to be away from wind in the spring and autumn and to be treated under conditions of constant heat. For these reasons, if under the direction of a physician, the patients can be treated and nursed at home or in a nearby hospital or clinic, the advantages of the therapy and medical care can be received with reduced difficulty and expense for the patient. In view of the above-mentioned facts, the dosage-forms of TMBL should be improved in order to offer MBL therapy to a greater number of patients.

In a paper by Jiuxi Jabu, "Observation of Therapeutic Effects of Tibetan Medicated Bath Liquor in 50 Cases of Rheumatoid Disease", in the Chinese Journal of Folk Medicine 1997, Vol. 3, No. 3, p. 18, it is reported that a bath liquor containing traditional pharmaceuticals, so called "Sweet Dew Bath with five flavor", was prepared with five kinds of traditional drugs, namely *Junipers clavaum* L., Rhododendron, *Myricaria germanica* (L.) Desv. Chinese Ephedra and Artemisia (wormwood). Its specific preparative method is as follows.

The above-mentioned five kinds of Chinese traditional medicines are collected. After cutting them into slices and then drying, distillers yeast is added for fermentation and they are air dried again. Several other kinds of traditional medicines may also be added, depending on the patient's condition and severity of the disease. The above-resulting mixture is put into a white cloth bag, soaked with water overnight and decocted. After the contents in the pot are concentrated to a half volume, the decocted liquor is poured into a vat and the drug bag is decocted once again into ⅓ of the original volume, and the decocted medicine liquid mixture is poured into the vat again. Decoction is repeated again to a volume of ⅓ of the original volume. The liquid from three decoctions is combined and mixed homogeneously with highland barley resulting in ready to use MBL.

Due to the fact that the volume of the medicated liquid is large and the time for production is long, even if such MBL could be obtained by industrial production, it would be difficult for patients to use at home. Hence, patients must be treated during hospitalization. Therefore, improvements in the dosage-form of the medicated bath liquor (MBL) are needed.

In the First Colloquium on Chinese Tibetan Drugs and Their Naturally Developing Strategy (Papers Collection, pp. 23–31), Li Fu-Yin Et al., there are reported preparative methods of TMBL. According to the article, a crude traditional medicine is selected, washed, cut into slices (5–10 mm), which are then put into a multi-functional extracting jar. Water is added in an amount of 10 times by weight of the total quantity of the crude medicine. Extraction under heat proceeds for one hour. Both volatile oil and a distillate containing volatile oil are filtered to obtain the 1st extract. Water is added to the drug residue in an amount 6 times the total volume of the crude medicine. Again, extraction proceeds under heat for another one hour and the liquid is then filtered to obtain the 2nd extract. Water is then added to the drug residue in an amount 4 times the total volume of the crude medicine. Extraction under heat proceeds for half an hour and the liquid is then filtered to obtain the 3rd extract. The three portions of extract are combined and concentrated under reduced pressure to form a paste extract. The latter is mixed homogeneously with volatile oil as well as a distillate containing volatile oil. A suitable stabilizer is added, along with auxiliary bath liquid, to the mixture which gives an ointment containing 2 g of crude medicine/ml, which can be diluted to form MBL. Although the advantage of this ointment formulation is that it decreases the volume, the water content of such an ointment is still more than 60%. This volume is too large and it renders transportation and application inconvenient. Besides, a certain amount of stabilizer is added which results in an increased amount of chemical constituents rendering the product more susceptible to mold. The above-mentioned drawbacks limit the development and practical application of TMBL therapy.

Because of the deficiencies of the liquid and ointment forms of MBL, studies on other dosage forms have been reported. For example, in Otkan Qimo et al. "An Exploration for Application and Improvement of Preparative Method of Mongolian Medicated Bath" in the Chinese Journal of National Medicine 1997, Vol. 3, No. 1, p. 29, a method for preparing a bath powder was disclosed. First of all, a number of crude medicines, which are not suitable for extraction, such as aromatic medicines, mineral medicines and animal medicines, etc., are selected and crushed. A series of botanical medicines, such as *Junipers clavaum* L., Artemisia (wormwood), Chinese Ephedra, *Myricaria germanica* (L.) Desv. *Rhododendron anthopogonoides* leaves are decocted and readied for use. First, the crude medicines are decocted for 2 hours (drug:water=1:5 by weight). The filtrates are collected and the residue is again decocted for 6 hours. Filtration and decoction are repeated 4–5 times until the medicine liquid is colorless and tasteless. Several batches of the medicine are combined and concentrated by heating. A paste is formed and laid out to cool. The crushed crude medicines, which are not suitable for boiling with water, are added. Then a powered substance is formed by stirring, baking and grinding. When used to treat a particular disease, 150–250 g (one dose per every person) of suitable medicine bath powder are mixed with water, stirred homogeneously and boiled. For use, it is put into a bathtub containing a suitable amount of warm water and is then stirred homogeneously. The advantages of the medicated bath powder are that it significantly decreases the weight and volume of the medicine needed so that it is more convenient to transport and use. However, the disadvantages are that the effective constituents could be destroyed during baking and the effective volatile constituents will volatilize to a certain degree and lose their effect. In addition, the crushed crude medicines, which are added during the last step of formulating, are boiled with water during use, which may not sufficiently release the effective constituents from the medicine.

DISCLOSURE OF THE INVENTION

The present invention provides a medicated bath powder that overcomes the drawbacks of conventional medicated bath formulations. The present invention provides a method of processing a MBL from natural plants into a medicated bath powder, which can be transported and applied conveniently. In addition, the therapeutic effects of the medicines are efficiently preserved in the formulation.

DETAILED DESCRIPTION OF THE INVENTION

The present invention provides a medicated bath powder processed from a medicated bath liquid (MBL), made from a natural plant, and methods of preparing thereof. The method comprises the steps of: 1) placing pre-treated natural plants in a vessel for extraction; adding water in an amount 5–15 times the total weight of the pre-treated natural plants; 3) performing the 1st extraction at a temperature from 70° C. to the boiling temperature for 0.5–24 hours and obtaining a volatile oil(VO1)and distillate containing a volatile oil (DVO); 4) filtering the 1st extraction mixture to obtain the 1st extract and 1st residue; 5) water is added to the 1st residue in an amount 3–10 times the total weight of the pre-treated natural plants; 6) performing the 2nd extraction at a temperature from 70° C. to the boiling temperature for 0.5–5 hrs; 7) filtering the 2nd extraction mixture to obtain the 2nd extract and 2nd residue; 8) water is added to the 2nd residue in an amount 3–10 times the total weight of the pre-treated natural plants; 9) performing the 3rd extraction at a temperature from 70° C. to the boiling temperature for 0.5–5 hrs; 10) filtering the 3rd extraction mixture to obtain the 3rd extract and 3rd residue; 11) combining the 1st, 2nd, and 3rd extracts and concentrating the mixed extracts under vacuum to form a concentrated drug liquor(CDL); 12) freeze drying the CDL under vacuum to form a solid medicine which is then ground to form a drug powder(DP), or spray drying the concentrated medicine extract to form a drug powder(DP); 13) subjecting the distillate containing the volatile oil(DVO) to an oil-water separation procedure to get a volatile oil(VO2), and 14) adding the VO1 and VO2 to the drug powder(DP) to obtain a homogeneous mixture.

The method of the present invention may further comprise a fourth extraction step. Water is added to the 3rd residue in an amount 3–10 times the total weight of the pre-treated natural plants, and the 4th extraction is performed at a temperature from 70° C. to the boiling temperature for 0.5–5 hrs. The 4th extraction mixture is filtered to obtain the 4th extract and 4th residue. The above steps 11 to 14 are repeated after four parts of extract are combined and concentrated under vacuum to form a concentrated drug liquor (CDL), which is then either freeze-dried under vacuum and then ground to form a drug powder(DP), or spray dried to form a drug powder(DP).

Preferably, the water added in the first step is in an amount 5–10 times the total weight of the pre-treated natural plants, and the first extraction is performed at a temperature from 70° C. to the boiling temperature for 1.5–6 hrs.

The pressure for concentrating the combined extracts is preferably between 0.01–0.09 Mpa, and more preferably between 0.01–0.06 Mpa. The temperature for concentrating the combined extracts under vacuum is preferably between 60° C.–90° C.

The combined extracts are preferably concentrated to $\frac{1}{10}$–$\frac{1}{2}$ the total volume of the combined extracts to form a concentrated medicated liquor(CML).

Preferably, when spray drying the concentrated medicated liquor, water steam is used as the spraying gas. The spraying pressure is preferably between 0.1–1.0 Mpa and the drying temperature is preferably between 60° C.–500° C., and more preferably between 200° C.–400° C. When freeze-drying the concentrated drug liquor, the pressure is preferably between 10–800 Pa, and the temperature for freeze-drying is preferably between –5° C. to –50° C. Preferably the water content in the final powdered drug is 5–10% by weight.

During spray-drying of the concentrated drug liquor to form a dried powdered drug, the concentrated drug liquor may be sprayed into a hot air chamber with a centrifugal spray. Hot air at 60° C.–400° C. is used as the drying medium. Under instantaneous heat exchange, the concentrated drug liquor can be dried to form a powdered drug. The temperature for the spray-drying is preferably between 200° C.–400° C.

Pretreatment of the raw materials from the natural plants is as follows. The crude drugs from natural plants are selected according to their qualified properties. They are washed with water, dried by air, and cut into 2–20 mm slices(5–10 mm slices are preferred). Some crude drugs must be soaked first, before extraction, in order to dissolve the drugs when extracting under heating. The soaking time depends on the properties of the crude drugs ror example, it is sufficient for some raw materials to soak for 30–40 min and others for 12–24 hours. Sometimes the water used for soaking can be utilized as a part of the water added to the first extraction. Medicated bath liquid (MBL) generally needs fermentation with yeast before use, because the therapeutic effects after fermentation will be better for treating rheumatic disease, postpartum convulsions, apoplectic sequel and dermatitis. The specific preparative method is as follows: the sliced crude drug is added to a steamer and boiled for 30–60 min. The contents in the steamer are removed and cooled to between 30° C.–40° C. After being mixed with yeast, the mixture stands for 48–72 hours at 30° C.–40° C. or until an alcohol smell appears. For example, six crude drugs, such as *Rhododendron anthopogonoides,* Mercurial Germanic (L.) Desv. *Juniperus clavaum* L., Chinese Ephedra, a kind of Artemisia, *Yanthoceras sorbifolia* Bunge, for treating rheumatoid arthritis, are fermented with yeast for 3 days. (See "Clinical Observation on 223 Cases of Rheumatoid arthritis by Treatment with Tibetan Drug Bath", (Chinese Journal of National Medicine) 1997, Vol. 3, No. 2, p. 15. Water used for the pretreatment may be tap water, well water, distilled water or ion-exchanged water.

The number of the extraction cycles depends on the properties of the botanical crude medicines selected. For example, for some botanical materials whose active ingredients are hard to extract, it is necessary to add water to the 3rd residue and perform a fourth extraction. Sometimes it is necessary to do a 5th, 6th and 7th extraction. However, if the active ingredients of the botanical materials are easily extracted with water, only a 1st extraction or a 1st and 2nd extraction are needed. The amount of water added is preferably 3–10 times the total volume of the crude material from the natural plants. The 4th extraction is preferably carried out at a temperature from 70° C. to the boiling temperature for 0.5–5 hrs. After combining all extracts, the extract mixture is concentrated under reduced pressure, lyophilized, ground or spray dried to form a drug powder (DP).

The container for extraction can be a decocting pot, or multi-function extracting pot, both of them having a water condenser. During the 1st extraction, a volatile oil(VO1) and distillate containing a volatile oil(DVO) are collected. The distillate containing the DVO is then subjected to an oil-water separation procedure to get a volatile oil(VO2). VO1 and VO2 are mixed into the medicine powder(DP) to obtain a homogeneous mixture, which turns into the final medicated bath powder of the present invention after freeze drying. If the crude material from a natural plant contains a low enough content of volatile oil so that it is not worth extracting, the procedures of collecting the volatile oil during extraction and then adding the volatile oil to the powdered drug can be omitted.

According to the method of the present invention, the medicated bath powder can be made from different natural plant materials, depending on which diseases are being treated.

In the powdered drugs prepared by the method of the present invention, every gram of powdered drug contains active ingredients equal to about 10 grams of the crude materials. The amount of active ingredients enriched in the final product of the present invention has greatly exceeded that made by conventional methods.

The method of the present invention also provides the following advantages.

The process of the present invention is more stable and predictable and product quality can be controlled, which can not be done using these previously-mentioned methods. The content of drug and active ingredient can be determined in order to guarantee the quality of the product, the powdered drug of TMBL.

Since the method of the present invention uses freeze drying under vacuum and spray-drying techniques, the active ingredients from the natural plants can be effectively preserved. In addition, the amount of active ingredients recovered from the crude material is greatly increased which gives a better therapeutic effect and allows for prolonged storage periods of the drugs.

No chemically synthetic stabilizers are added to the powdered drug prepared by the method of the present invention. Therefore, it is safe and convenient to use. Thus, the present invention provides for improved of dosage forms of TMBL.

The following examples are used only to further illustrate the present invention but are not intended to produce any limitation to the present invention.

EXAMPLE 1

Preparation of a medicated bath power for the treatment of arthralgia-syndrome.

Crude materials from the natural plants in this prescription are: Acanthopanax Bark (20 g), *Piper kadsura* (choisy) Ohwi (20 g), Tou Feng Cao (a kind of herb)(20 g), Angelica (10 g), Green Tangerine Peel (10 g), Papaya(10 g), and *Lycopodium clavatum* L(10 g).

The above-mentioned botanical crude materials are pretreated as follows.

The selected crude materials are washed in water and dried in air, then cut into 6 mm slices and soaked in water for 12 hrs. The pretreated crude materials are then put into a multi-functional extracting pot. The water used for the first extraction is well water used for drinking. Water is added in an amount 3,5,9 or 10 times the total weight of the crude materials.

The 1st extraction is carried out at a temperature from 70° C. to the boiling temperature for ½, 3 or 5 hrs. After the 1st extraction, a volatile oil(VO1), a distillate containing a volatile oil(DCV), the 1st extract and 1st drug residue are collected. The DCV is then subjected to a oil-water separation process and the obtained volatile oil(VO2) is mixed with VO1 and loaded in a bottle. Water is then added to the I st drug residue in an amount 3, 5 or 10 times the total weight of crude materials. The 2nd extraction is carried out at a temperature from 70° C. to the boiling temperature for ½, 1.5 or 5 hrs, which results in the 2nd extract and 2nd drug residue. Water is then added to the 2nd residue in an amount 3, 5 or 10 times the total weight of crude materials. The 3rd extraction is carried out at a temperature from 70° C. to the boiling temperature for ½, 1 or 5 hrs, which results in the 3rd extract and 3rd drug residue. Optionally, water may be added into the 3rd residue in an amount 3, 5 or 10 times the total weight of crude drugs. A 4th extraction with water can then be carried out at a temperature from 70° C. to the boiling temperature. All extracts are collected, combined and concentrated under reduced pressure from 0.05 Mpa to 0.09 Mpa and a temperature from 60 to 90° C. to obtain a drug liquor which is then concentrated to ⅒, ⅕ or ½ of the original volume of the combined extracts. The drug liquor is freeze-dried under vacuum to form a solid drug at a pressure of 10 Pa, 30 Pa or 800 Pa, and a temperature of –5° C., –10° C. or –50° C. The water content of the formed solid drug is 5%, 6.1% or 10% of the total weight of the solid drug. The solid drug is then ground to form a drug powder, which is then mixed with VO1 and VO2 which results in the medicated bath powder for the treatment of arthralgia syndrome.

EXAMPLE 2

Using the preparative method provided by the present invention to prepare a drug bath powder for treating rheumatism, rheumatoid arthritis and skin disease:

This example illustrates the preparation of medicated bath powder from a medicated bath medicine prescription used by Tibetan physicians to treat rheumatism, rheumatoid disease and skin disease. The raw materials from the natural plants of this prescription are: Rhododendron 100 g, Artemisia Sieversiana Exhart ex Willd 100 g, Chinese Ephedra 100 g, *Juniperus clavaum* L. 100 g and *Myricaria germanica* (L.) Desv. 100 g.

The botanical raw materials are pretreated as follows. The qualified raw materials are selected, washed, dried, cut into about 6 mm slices and boiled for 40 min. The raw materials are cooled to 35° C., mixed with a suitable amount of yeast and maintained at 35° C. for 60 hrs or until an alcohol smell appears.

The pretreated materials are then subjected to the same heat extraction procedures as described in Example 1. After three cycles of heat extraction as in Example 1, the three extracts are combined, concentrated under reduced pressure at 0.03 Mpa at 65° C.±5° C. forming a concentrated drug liquor. After the drug liquor is concentrated to a volume ⅓ (circa) of the combined extracts, spray-drying is carried out to form a solid drug. Water steam is applied as the nebulization gas under a pressure of 0.1 Mpa, 0.4 Mpa or 1.0 Mpa. The temperature for spray-drying is 60° C. 200° C. 400° C. or 500° C. The dried solid drug is then ground into a drug powder. Alternatively, the concentrated drug liquor can be sprayed into a hot air chamber by centrifugal spray, using 60° C.–400° C. hot air as the drying medium. Under instantaneous heat exchange, the concentrated drug liquor is dried to form a powdered drug. The powdered drug is then mixed with volatile oil(VO1+VO2) to form the medicated bath powder for the treatment of rheumatism, rheumatoid arthritis and skin diseases.

EXAMPLE 3

Preparation of a Medicated Bath Powder for Treating Skin Diseases.

The preparative and operative procedures are basically identical to those as described in Example 1, except that the drug components and diseases to be treated are different. This example illustrates a prescription of medicated bath liquor used by Tibetan physicians to treat skin diseases. In this prescription the crude drugs from natural plants include: Sapium Sebiferum (L.) Roxb 60 g, fresh Cinnamomum Camphora (L.) Presl, 60 g, Pine leaves 60 g, Ginger 60 g.

The botanical crude drugs are pretreated as follows. The crude drugs are washed, dried, and cut into approximately 9 mm slices. The pretreated crude drugs from natural plants are placed in a multifunctional pot and water is added in an amount 10 times the total weight of the crude drugs. The 1st extraction under heat is carried out at the boiling temperature for 6 hrs. After the first filtration, the 1st extract, 1st residue, volatile oil(VO1) and distillate containing volatile oil(DCV) are obtained. The DCV is then subjected to an oil-water separation procedure and which results in a volatile oil(VO2) which is mixed with VO1. Water is added to the 1st residue in an amount 7 times the total weight of the crude drugs. The 2nd extraction under heat is carried out at the boiling temperature for 1.5 hrs and the 2nd extract and 2nd residue are obtained. Water is added to the 2nd residue in an amount 4 times the total weight of the crude drugs. The 3rd extraction under heat is carried out at the boiling temperature for 0.7 hr and the 3rd extract is obtained. The 1st, 2nd, and 3rd extracts are combined and concentrated under 0.07 Mpa, at a temperature of 70° C.±5° C. After the drug liquor is concentrated to a volume 0.15 times that of the combined extracts, freeze-drying under vacuum is carried out to form the solid drug. The pressure for freeze-drying under vacuum is 50 Pa and the is −25° C. The water content of the formed solid drug powder is 7%. The solid drug formed by freeze-drying under vacuum is ground to form a drug powder. Finally, the volatile oil mixture(VO1+VO2) is added into the drug powder and the product is mixed homogeneously to result in the drug bath powder for treating skin diseases.

I claim:

1. A method of processing a mixture of natural plants into a medicated bath powder, comprising the steps of:

i mixing and pretreating an effective amount of the natural plants selected from the group consisting of Acanthopanax Bark, Piper Kadsura Ohwi, Tou Feng Cao, Angelica, Green Tangerine Peel, Papaya and *Lycopodium clavatum* L, Rhododendrons, Artemisia Sieversiana Exhart ex Willol, Chinese Ephedra, *Juniperus clavaum* L, *Myricaria germani-ca* Desv, mixtures of Sapium Sebiferum, Roxb, fresh Cinnamomum Camphora, Presl, Pine leaves and Ginger to obtain a crude drug mixture;

ii placing the crude drug mixture in a vessel and adding water in an amount 5–15 times the total weight of the crude drug mixture;

iii performing the 1st extraction at a temperature from 70° C. to the boiling temperature for 0.5–24 hours and obtaining a volatile oil(VO1) portion, a distillate containing the volatile oil(DVO) and a 1st extraction mixture;

iv filtering the 1st extraction mixture to obtain the 1st extract and 1st residue;

v adding water to the 1st residue in an amount 3–10 times the total weight of the crude drugs;

vi performing the 2nd extraction at a temperature from 70° C. to the boiling temperature for 0.5–5 hrs and filtering the 2nd extraction mixture to obtain the 2nd extract and 2nd residue;

vii adding water to the 2nd residue in an amount 3–10 times the total weight of the crude drugs;

viii performing the 3rd extraction at a temperature from 70° C. to the boiling temperature for 0.5–5 hrs and filtering the 3rd extraction mixture to obtain the 3rd extract and 3rd residue;

ix combining the 1st, 2nd, and 3rd extracts and concentrating the mixed extracts, under vacuum, to form a concentrated drug liquor(CDL);

x freeze drying the CDL, under vacuum, to form a solid medicine which is then ground to form a drug powder (DP), or spray dried to form a drug powder(DP);

xi subjecting the distillate containing a volatile oil(DVO) to an oil-water separation procedure to get a volatile oil(VO2), xii mixing VO1 and VO2 with the drug powder(DP) to obtain a homogeneous medicated bath powder.

2. The method according to claim 1, further comprising a 4th extraction step by adding water to the 3rd residue in an amount 3–10 times the total weight of the crude drugs; performing the 4th extraction at a temperature from 70° C. to the boiling temperature for 0.5–5 hrs and filtering the 3rd extraction mixture to obtain the 4th extract and 4th residue.

3. The method according to claim 1, wherein the 1st extraction is carried out for 1:5–6 hrs.

4. The method according to claim 1, wherein the pressure for concentrating the combined extracts under reduced pressure is between 0.01–0.09 Mpa and the temperature is 60° C.–90° C.

5. The method according to claim 4, wherein the pressure for concentrating the combined extract under reduced pressure is between 0.01–0.06 Mpa.

6. The method according to claim 4, wherein the volume of the concentrated drug liquor is 0.1 to 0.5 the volume of the combined extracts.

7. The method according to claim 2, wherein the pressure for concentrating the combined extracts under reduced pressure is between 0.01–0.09 Mpa and the temperature is 60° C.–90° C.

8. The method according to claim 7, wherein the pressure for concentrating the combined extract under reduced pressure is between 0.01–0.06 Mpa.

9. The method according to claim 7, wherein the volume of concentrated drug liquor is 0.1–0.5 the volume of the combined extracts.

10. The method according to claim 1, wherein the spray drying is performed by using water steam as the spraying gas, at a pressure between 0.1–1.0 Mpa and a temperature between 60° C.–500° C.

11. The method according to claim 1, wherein the pressure for freeze-drying the concentrated medicated liquor under vacuum is between 10–800 Pa and the temperature is −5° C.–−50° C.

12. The method according to claim 1, wherein the water content of the powdered drug is 5–10% of the weight if the powdered drug.

13. The method according to claim 1, wherein the concentrated drug liquor is spray dried to form a powdered drug by spraying the drug liquor into hot air chamber with a centrifugal sprayer, at a temperature between 60° C.–400° C.

14. The method according to claim 10, wherein the the temperature for spray drying the concentrated drug liquor to form a powdered drug is between 60° C.–400° C.

* * * * *